United States Patent [19]

McEvoy et al.

[11] 4,125,732
[45] Nov. 14, 1978

[54] 2-ARYLOXY-2-(PHENOXYALKOXY)PHENYL ACETIC ACID AND ESTERS

[75] Inventors: Francis J. McEvoy, Pearl River; Jay D. Albright, Nanuet, both of N.Y.

[73] Assignee: American Cyanamid Company, Stamford, Conn.

[21] Appl. No.: 794,510

[22] Filed: May 6, 1977

[51] Int. Cl.$^2$ .................. C07C 65/14; C07C 69/76
[52] U.S. Cl. .................. 560/62; 260/410.9 R; 260/413; 260/465D; 260/501.16; 560/56; 560/59; 560/61; 424/308; 424/317; 424/318

[58] Field of Search ........ 260/520 C, 465 D, 410.9 R, 260/413, 501.16; 560/62, 61, 56, 59

[56] References Cited

FOREIGN PATENT DOCUMENTS 755,105  3/1967  Canada ........................ 260/520 C Primary Examiner—Jane S. Myers
Attorney, Agent, or Firm—Edward A. Conroy, Jr.

[57] ABSTRACT

This disclosure describes substituted 2-aryloxy-2-(para-phenoxyalkoxy)phenylacetic acids and esters and salts thereof useful as hypolipidemic agents.

13 Claims, No Drawings

2-ARYLOXY-2-(PHENOXYALKOXY)PHENYL ACETIC ACID AND ESTERS

BRIEF SUMMARY OF THE INVENTION

This invention relates to new organic compounds and, more particularly, is concerned with novel substituted 2-aryloxy-2-(para-phenoxyalkoxy)phenylacetic acids and esters which may be represented by the following structural formula:

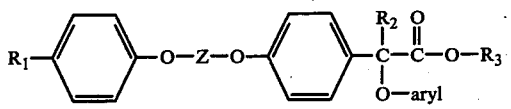

wherein $R_1$ is fluoro, chloro, trifluoromethyl or tert.-butyl; $R_2$ is hydrogen or straight chain alkyl having up to 6 carbon atoms; $R_3$ is hydrogen or alkyl having up to 4 carbon atoms; Z is a divalent radical of the formulae:

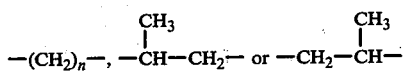

wherein $n$ is the integer 1,2 or 3; and aryl is 3,4-dimethylphenyl, 3-methyl-4-chlorophenyl, 2-chloro-4-tert.-butylphenyl, 5-indanyl, 5,6,7,8-tetrahydro-2-naphthyl or moieties of the formulae:

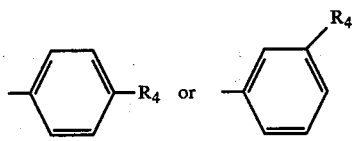

wherein $R_4$ is hydrogen, chloro, cyano, alkyl having up to 4 carbon atoms, trifluoromethyl, phenoxy, benzyloxy or cyclohexyl. The invention also includes novel compositions of matter containing the above-defined compounds useful as hypolipidemic agents and the method of lowering serum sterol levels and serum triglyceride levels in mammals therewith.

BACKGROUND OF THE INVENTION

Considerable effort has been directed in recent years to obtain substances which are useful in the treatment of hyperlipidemia, a condition associated with elevated cholesterol, phospholipid and/or triglyceride blood levels. This condition is associated with a number of diseases, one of the most serious being atherosclerosis. Medicaments used to lower cholesterol, phospholipid and triglyceride blood levels are termed hypolipidemic drugs. Presently three major lipid-lowering agents are available; clofibrate, D-thyroxine, and nicotinic acid. [R. I. Levy and D. S. Fredrickson, Post-graduate Medicine, Vol. 47, pps. 130-136 (1970).] Reduction of serum sterol is highly desirable clinically since essentially all major studies reported in the literature indicated that elevated serum sterol concentration is directly related to the development of atherosclerosis. Of the clinical types of hyperlipoproteinemias described to date, the major lipids found in abnormal levels are sterol and triglycerides. The compounds of this invention are capable of decreasing both of these blood lipid fractions as well as phospholipids, the third major lipid moiety in blood.

DETAILED DESCRIPTION OF THE INVENTION

The novel compounds of the present invention are generally obtainable as white to pale yellow crystalline materials having characteristic melting points and which may be purified by recrystallization from common organic solvents such as methanol, ethanol, hexane, ethyl acetate, and the like. Some of the novel compounds of the present invention are only obtainable as colorless, pale yellow or tan oils having characteristic absorption spectra. The novel compounds of the present invention are appreciably soluble in polar organic solvents such as chloroform, dimethylformamide, dimethylsulfoxide, and the like but are relatively insoluble in water.

The cationic salts of the compounds when $R_3$ is hydrogen are, in general, white to yellow crystalline solids having characteristic melting points and absorption spectra. They are relatively soluble in water, methanol and ethanol but are relatively insoluble in non-polar organic solvents such as benzene and diethyl ether.

Also embraced within the scope of the present invention are the non-toxic, pharmaceutically acceptable salts of the novel compounds of the present invention when $R_3$ is hydrogen. The cations comprised in these salts include, for example, the non-toxic metal cations such as the sodium ion, potassium ion, calcium ion, and magnesium ion as well as amine salts with organic bases such as ammonia, methylamine, dimethylamine, tri (lower alkyl) amines (e.g., trimethylamine, triethylamine, etc.), pyridine, piperidine, 2-hydroxyethylamine, tris(2-hydroxyethyl)-amine, procaine, and the like.

The novel compounds of the present invention may be readily prepared in accordance with the following reaction scheme:

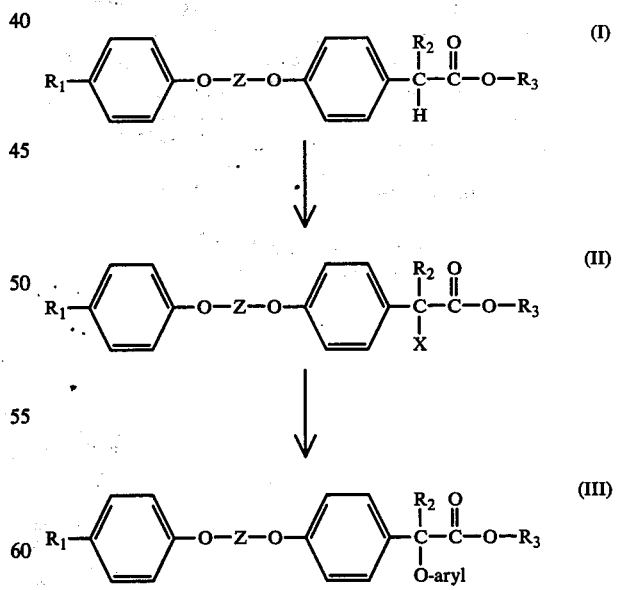

wherein X is chloro or bromo and $R_1$, $R_2$, $R_3$, Z and aryl are as hereinabove defined. In accordance with the above reaction scheme, an appropriately substituted 2-(para-phenoxyalkyoxy)phenylacetic acid or ester (I) is treated with a halogenating agent to provide the intermediate 2-halo-2-(para-phenoxyalkoxy)phenylacetic acid or ester (II). This α-halogenation of the starting materials (I) may be carried out with reagents such as N-chlorosuccinimide, N-bromosuccinimide, chlorine, bromine, sulfuryl chloride, and the like. The α-halogenations with N-chlorosuccinimide and N-bromosuccinimide are best carried out on the esters (I, $R_3$=lower alkyl) by heating at the reflux temperature in inert solvents such as dichloromethane, chloroform, carbon tetrachloride, and the like. The reaction may be catalyzed by the addition of hydrogen chloride in the N-chlorosuccinimide halogenation and hydrogen bromide in the N-bromosuccinimide halogenation. The halogenations are generally complete with 3–24 hours although some halogenations may require longer reaction times. These α-halogenations may also be catalyzed with heavy metals such as, for example, nickel and thallium salts. The α-halo intermediates (II) may also be prepared by reacting the acids (I, $R_3$=hydrogen) with thionyl chloride or other acid chloride forming reagent to give the corresponding acid chlorides and then halogenating with N-chlorosuccinimide, N-bromosuccinimide, chlorine, bromine, or sulfuryl chloride to give the 2-halo-2-(para-phenoxyalkoxy)phenylacetic acid chlorides. Reaction of these with lower alkanols gives the intermediates (II, $R_3$=lower alkyl) while reaction with water gives the intermediates (II, $R_3$=hydrogen).

The intermediates (II) are reacted with phenolic compounds of the formula aryl-OH wherein aryl is hereinabove defined to give the novel compounds (III) of the present invention. This reaction is conveniently carried out in an inert solvent such as a lower alkanol, dimethylsulfoxide, N,N-dimethylformamide, N,N-dimethylacetamide, xylene, toluene, tetrahydrofuran, hexamethylphosphoramide, and the like at the reflux temperature thereof in the presence of a base to first convert the phenolic compound to the corresponding phenoxide. Bases such as sodium lower alkoxides, sodium hydride, sodium carbonate, potassium carbonate, and the like may be used for the preparation of the phenoxides. The displacement of the α-halogen atom by an appropriate phenol is best carried out in refluxing tetrahydrofuran, refluxing methanol, or refluxing methanol/benzene for 3–24 hours with sodium methoxide or sodium hydride as the base. Alternatively, the displacement reaction may be carried out in refluxing acetone for 5–30 hours with potassium carbonate as the base.

The novel esters of the present invention (III, $R_3$=lower alkyl) may be readily prepared by reaction of the acid chlorides (IV) with an appropriate lower alkanol.

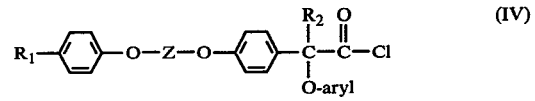

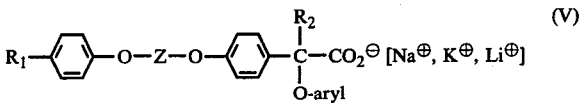

Alternatively, the novel esters of the present invention (III, $R_3$=lower alkyl) may be prepared by reaction of a methyl ester (III, $R_3$=methyl) with another lower alkanol in an ester exchange reaction. Reaction of an appropriate lower alkyl halide with a carboxylic acid salt (V) is also productive of the novel esters of the present invention. This reaction is best carried out in a solvent such as hexamethylphosphoramide at a temperature range of about 50°–150° C. for a period of time of 1 to 18 hours or more.

The mechanism of action of the 2-aryloxy-2-(para-phenoxyalkoxy)phenylacetic acids and esters of the present invention is not known. However, the novel compounds of the present invention possess hypolipidemic activity as determined by animal experiments as follows. The compounds to be studied are administered orally admixed with the diet to groups of 2–6 male rats, Cobs CD from Charles River. A control group of 6–8 rats is maintained on the diet alone. Test groups are maintained on the diet plus the indicated percentage of compound by weight. After 5 days treatment, serum sterol concentrations are determined by an automated method based on the procedure of J. Levine and B. Zak, Clin. Chem. 10, 381 (1964). Serum triglycerides are estimated by an automated method based on the procedure of R. P. Noble and F. M. Campbell, Clin. Chem. 16, 166 (1970). In these tests, a compound is considered to have hypolipidemic activity if it depresses serum sterol levels 15% or more below that of the controls and/or depresses serum triglyceride levels by 25% or more below controls. In Table I below is set forth the results obtained in this test with typical compounds of the present invention at a dosage level in the diet of 0.1% by weight.

TABLE I

| Compound | Dose % In Diet | % Lowering Sterol | % Lowering Triglyceride |
|---|---|---|---|
| Methyl(p-chlorophenoxy){p-[(p-chlorophenoxy)methyoxy]phenyl}acetate | 0.1 | 36 | 37 |
| Methyl(p-tert.-butylphenoxy){p-[(p-chlorophenoxy)methoxy]phenyl}acetate | 0.1 | 31 | 53 |
| (3,4-Dimethylphenoxy){p-[(p-chlorophenoxy)methoxy]phenyl}acetic acid | 0.1 | 37 | 64 |
| (m-tert.-Butylphenoxy){p-[(p-chlorophenoxy)methoxy]phenyl}acetic acid | 0.1 | 20 | 52 |
| (α,α,α-Trifluoro-p-tolyloxy){p-[(p-chlorophenoxy)methoxy]phenyl}acetic acid | 0.1 | 27 | 62 |
| [p-(Benzyloxy)phenoxy]{p-[(p-chlorophenoxy)methoxy]phenyl}acetic acid | 0.1 | 19 | 72 |
| (α,α,α-Trifluoro-m-tolyloxy){p-[(p-chlorophenoxy)methoxy]phenyl}acetic acid | 0.1 | 18 | 54 |
| Methyl(p-tert.-butylphenoxy){p-[2-(p-tert.-butylphenoxy)ethoxy]phenyl}acetate | 0.1 | 17 | 50 |
| Methyl(p-chlorophenoxy){p-[2-(p-chlorophenoxy)ethoxy]phenyl}acetate | 0.1 | 18 | 31 |
| Methyl(p-cyclohexylphenoxy){p-[2-(p-chlorophenoxy)ethoxy]phenyl}acetate | 0.1 | 8 | 53 |
| Methyl(α,α,α-trifluoro-p-tolyloxy){p-[2-(p-chlorophenoxy)ethoxy]phenyl}acetate | 0.1 | 25 | 70 |

TABLE I-continued

| Compound | Dose % In Diet | % Lowering Sterol | % Lowering Triglyceride |
|---|---|---|---|
| (p-tert.-Butylphenoxy){p-[2-(p-chlorophenoxy)propoxy]phenyl}acetic acid | 0.1 | 25 | 58 |
| Methyl(p-tert.-butylphenoxy){p-[3-(p-chlorophenoxy)propoxy]phenyl}acetate | 0.1 | 33 | 55 |
| Methyl(p-chlorophenoxy){p-[3-(p-chlorophenoxy)propoxy]phenyl}acetate | 0.1 | 15 | 50 |
| Methyl(4-chloro-3-methylphenoxy){p-[3-(p-chlorophenoxy)propoxy]phenyl}acetate | 0.1 | 14 | 51 |
| Methyl(5-indanyloxy){p-[3-(p-chlorophenoxy)propoxy]phenyl}acetate | 0.1 | 15 | 47 |
| Methyl(p-benzyloxyphenoxy){p-[3-(p-chlorophenoxy)propoxy]phenyl}acetate | 0.1 | 14 | 49 |
| Methyl(p-phenoxyphenoxy){p-[3-(p-chlorophenoxy)propoxy]phenyl}acetate | 0.1 | 22 | 49 |
| Methyl(p-cyclohexylphenoxy){p-[3-(p-chlorophenoxy)propoxy]phenyl}acetate | 0.1 | 11 | 50 |
| Methyl($\alpha,\alpha,\alpha$-trifluoro-p-tolyloxy){p-[3-(p-chlorophenoxy)propoxy]phenyl}acetate | 0.1 | 20 | 53 |
| [p-(Benzyloxy)phenoxy]{p-[3-(p-chlorophenoxy)propoxy]phenyl}acetic acid | 0.1 | 41 | 64 |
| (5,6,7,8-Tetrahydro-2-naphthyloxy){p-[3-(p-chlorophenoxy)propoxy]phenyl}acetic acid | 0.1 | 19 | 40 |
| ($\alpha,\alpha,\alpha$-Trifluoro-m-tolyloxy){p-[3-(p-chlorophenoxy)propoxy]phenyl}acetic acid | 0.1 | 21 | 31 |
| (m-Chlorophenoxy){p-[3-(p-chlorophenoxy)propoxy]phenyl}acetic acid | 0.1 | 18 | 21 |
| ($\alpha,\alpha,\alpha$-Trifluoro-p-tolyloxy){p-[2-(p-chlorophenoxy)propoxy]phenyl}acetic acid | 0.1 | 19 | 51 |
| (p-Chlorophenoxy){p-[2-(p-chlorophenoxy)propoxy]phenyl}acetic acid | 0.1 | 25 | 58 |
| (p-tert.-Butylphenoxy){p-[2-(p-chlorophenoxy)-1-methylethoxy]phenyl}acetic acid | 0.1 | 28 | 67 |
| ($\alpha,\alpha,\alpha$-Trifluoro-p-tolyoxy){p-[2-(p-chlorophenoxy)-1-methylethoxy]phenyl}acetic acid | 0.1 | 28 | 39 |

The novel compounds of the present invention have been found to be highly useful as hypolipemic agents in mammals when administered orally in amounts ranging from about 5 mg. to about 300 mg. per kg of the body weight per day. A preferred dosage regimen for optimum results would be from about 2 mg. to about 30 mg. per kg of the body weight per day, and such dosage units are employed that a total of from about 35 mg. to about 2.8g of compound for a subject of about 70 kg. body weight are administered in a 24 hour period.

The hypolipemic compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the mixtures may be incorporated with excipients and used in the form of tablets, troches, capsules, elixirs, suspensions, syrups, wafers, and the like. Such compositions and preparations should contain at least 0.1% of hypolipemic agent. The percentage of active ingredient in the compositions and preparations may, of course, be varied and may conveniently be between about 5% to about 25% of the weight of the unit. The amount of mixture in such therapeutically useful compositions is such that a suitable dosage will be obtained. Preferred compositions or preparations according to the present invention are prepared so that an oral dosage unit form contains between about one and 500 mg. of hypolipemic agent.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active mixtures, sucrose as a sweetening agent, methyl and propylparabens as preservations, a dye and flavoring such as cherry or orange flavor. Of course, any material used in preparing any dosage unit form should be pharmaceutically pure and substantially nontoxic in the amounts employed.

A preferred embodiment of the present invention may be represented by formula (III) wherein $R_1$ is chloro or tert.-butyl; $R_2$, $R_3$, and Z are as hereinabove defined; and aryl is a moiety of the formulae:

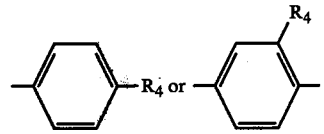

wherein $R_4$ is tert.-butyl, trifluoromethyl, phenoxy or benzyloxy.

This invention will be described in greater detail in conjunction with the following specific examples. The following examples are given for the purpose of illustration and are not intended to limit the scope of the invention.

EXAMPLE 1 Methyl {p-[(p-chlorophenoxy)methoxy]phenyl}acetate

A 16.6 g sample of sodium hydride oil dispersion (60% NaH) is washed several times with hexane. To the sodium hydride is added 340 ml of N,N-dimethylacetamide and a solution of 69 g of methyl (p-hydroxyphenyl)acetate in 120 ml of N,N-dimethylacetamide is added dropwise. The mixture is stirred at room temperature under argon for 1 hour and then at 50° C. for 30 minutes. A 68 g portion of potassium iodide and 20 ml of hexamethylphosphoramdide is added followed by the dropwise addition of 73.2 g of p-chlorophenoxymethyl chloride in 175 ml of N,N-dimethylacetamide. The mixture is stirred and heated (oil bath) at 100° C. for 18 hours. To the mixture at room temperature is added dropwise 3 liters of water containing 60 ml of acetic acid. The mixture is stirred and chilled in an ice bath for 1 hour, filtered and the solid washed with water to give the product.

A 36 g sample is dissolved in 130 ml of methanol and treated with activated charcoal, the mixture is filtered and the filtrate chilled to give 14.2 g of product as white crystals. Recrystallization from ether-petroleum ether gives white crystals, mp 45°–47° C.

EXAMPLE 2

Methyl bromo{p-[(p-chlorophenoxy)methoxy]phenyl}acetate

To a solution of 23.3 g of methyl{p-[(p-chlorophenoxy)methoxy]phenyl}acetate in 300 ml of carbon tetrachloride is added 14.2 g of N-bromosuccinimide. The mixture is stirred and refluxed for 24 hours or until reaction is complete. The mixture is cooled, filtered and the filtrate poured through a column of silica gel (60–200 mesh). Cuts (250 ml) are taken with carbon tetrachloride eluent. The product is collected in fractions 2–6 to give 25.5 g of product as an oil.

EXAMPLE 3

Methyl (p-chlorophenoxy){p-[(p-chlorophenoxy)methoxy]phenyl}acetate

To a solution of 2.74 g of p-chlorophenol in 25 ml of tetrahydrofuran is added 0.85 g of 60% sodium hydride-oil dispersion. After stirring under argon at room temperature for 1 hour, 3.52 g of potassium iodide and 1 ml of hexamethylphosphoramide is added. To the mixture is added dropwise, a solution of 8.18 g of methyl bromo{p-[(p-chlorophenoxy)methoxy]phenyl}acetate in 45 ml of tetrahydrofuran. The mixture is refluxed for 18 hours. The mixture is poured into 500 ml of ice and water containing 2 ml of acetic acid. The mixture is extracted with ether and the ether extracts are washed with sodium chloride solution, sodium bicarbonate solution and with sodium chloride solution. The extract is dried (MgSO$_4$) and the solvent removed under reduced pressure to give the product (9.5 g) as a viscous oil. Chromatography over silica gel with dichloromethane as eluent gives 7.6 g of gum which is crystallized from methanol to give 5.8 g of the product as white crystals. Recrystallization from methanol gives white crystals, mp 64°–65° C.

EXAMPLE 4

Methyl(p-tert.-butylphenoxy){p-[(p-chlorophenoxy)methoxy]phenyl}acetate

As described in Example 3, 8.92 g of methyl bromo{p-[(p-chlorophenoxy)methoxy]phenyl}acetate, 3,45 g of p-tert.-butylphenol and 9.17 g of 60% sodium hydride-oil dispersion are reacted in 75 ml of tetrahydrofuran containing 1 ml of hexamethylphosphoramide and worked-up to give 11 g of product as an oil. Chromatography over silica gel with dichloromethane as eluent gives 7.1 g of gum which is crystallized from methanol to give 4.9 g of white crystals. Recrystallization gives white crystals, mp 64°–65° C.

EXAMPLE 5

Methyl (α,α,α-trifluoro-p-tolyloxy){p-[(p-chlorophenoxy)methoxy]phenyl}acetate

To a mixture of 3.63 g of α,α,α-trifluoro-p-cresol in 30 ml of tetrahydrofuran under argon is added 0.895 g of 60% sodium hydride-oil dispersion. The mixture is stirred at room temperature for 75 minutes. To the mixture is added 3.72 g of potassium iodide and 1 ml of hexamethylphosphoramide followed by the dropwise addition of a solution of methyl bromo{p-[(p-chlorophenoxy)methoxy]phenyl}acetate in 40 ml of tetrahydrofuran. The mixture is refluxed for 18 hours and poured into 500 ml of water containing 2 ml of acetic acid. The mixture is extracted with ether and the extracts washed with sodium chloride, 10% sodium bisulfite and with saturated sodium chloride solution. After drying (MgSO$_4$) the solvent is removed under reduced pressure to give 10.5 g of a gum. Chromatography over silica gel with dichloromethane as eluent gives 9.4 g of product as a gum.

EXAMPLE 6

(α,α,α-Trifluoro-p-tolyloxy){p-[(p-chlorophenoxy)methoxy]phenyl}acetic acid

To a solution of 8.5 g of methyl(α,α,α-trifluoro-p-tolyloxy){p-[(p-chlorophenoxy)methoxy]phenyl}acetic acid in 50 ml of ethanol is added a solution of 6 g of potassium hydroxide in 50 ml of water. The mixture is refluxed for 4 hours and while hot, is acidified with 10 ml of concentrated HCl. The mixture is chilled immediately and extracted with dichloromethane. The extract is washed with a solution of sodium chloride, dried (MgSO$_4$) and the solvent is removed under reduced pressure. The residue is triturated with hexane containing small amounts of ether and dichloromethane and chilled to give 6.7 g of product as white crystals. The product is recrystallized by dissolving in 50 ml of benzene, filtering the solution and diluting the filtrate with 75 ml of hexane. Chilling and filtering gives 6.1 g of white crystals, mp 88°–89° C.

EXAMPLE 7

Methyl(m-tert.-butylphenoxy){p-[(p-chlorophenoxy)methoxy]phenyl}acetate

A mixture of 3.3 g of 3-tert.-butylphenol and 0.83 g of 60% sodium hydride-oil dispersion in 40 ml of tetrahydrofuran is stirred under argon for 1 hour at room temperature. To the mixture is added 3.65 g of potassium iodide, one ml of hexamethylphosphoramide and dropwise, a solution of 8.51 g of methyl bromo{p-[(p-chlorophenoxy)methoxy]phenyl}acetate in 30 ml of tetrahydrofuran. The mixture is refluxed for 18 hours and poured into 500 ml of water containing 2 ml of acetic acid. The mixture is extracted with ether and the ether extracts washed with sodium bicarbonate solution, 10% sodium bisulfite solution and with saturated sodium chloride solution. The solvent is removed under reduced pressure to give 11.7 g of a gum. Chromatography over silica gel with dichloromethane as eluent gives 6 g of product as a gum.

EXAMPLE 8

(m-tert.-Butylphenoxy){p-[(p-chlorophenoxy)methoxy]phenyl}acetic acid

To a solution of 9.5 g of methyl(m-tert.-butylphenoxy){p-[(p-chlorophenoxy)methoxy]phenyl}acetate in 60 ml of ethanol is added a solution of 7 g of potassium hydroxide in 60 ml of water. The mixture is stirred and refluxed for 18 hours and while hot is acidified with 11.5 ml of concentrated HCl. The mixture is chilled immediately. The supernatant is decanted from the oil which separates. Water is added and decanted. The gummy material is dissolved in dichloromethane, dried (MgSO$_4$) and the solvent removed under reduced pressure to give 8.4 g of a gum. The gum is triturated with hexane containing a small amount of dichloromethane to give 5.7 g of yellow crystals. The crystals are dissolved in 25 ml of dichloromethane and the solution diluted with 50 ml of hexane. Chilling gives 4.4 g of product as pale yellow crystals, mp 122°–124° C.

EXAMPLE 9

Methyl(3,4-dimethylphenoxy){p-[(p-chlorophenoxy)methoxy]phenyl}acetate

A mixture of 2.70 g of 3,4-dimethylphenol and 0.89 g of 60% sodium hydride-oil dispersion in 40 ml of tetrahydrofuran is stirred at room temperature for 1 hour. To the mixture is added 3.7 g of potassium iodide, 1 ml of hexamethylphosphoramide and dropwise a solution of 8.55 g of methyl bromo{p-[(p-chlorophenoxy)methoxy]phenyl}acetate in 30 ml of tetrahydrofuran. The mixture is refluxed for 18 hours and worked-up as described in Example 5 to give 10.4 g of a gum. Chromatography over silica gel with dichloromethane as eluent gives the product as a gum.

EXAMPLE 10

(3,4-Dimethylphenoxy){p-[(p-chlorophenoxy)methoxy]phenyl}acetic acid

A solution of 8.1 g of methyl(3,4-dimethylphenoxy){p-[(p-chlorophenoxy)methoxy]phenyl}acetate and 6 g of potassium hydroxide in 100 ml of ethanol:water (1:1) is refluxed for 4 hours. The mixture is acidified while hot with 10 ml of concentrated HCl and immediately cooled in an ice bath. The supernatant is decanted from the oil which separates and water is added and decanted. The residue is dissolved in dichloromethane, the solution dried (MgSO$_4$) and the solvent removed under reduced pressure to give 7.7 g of a gum. Trituration with hexane containing a small amount of ether gives 5.9 g of product as yellow crystals. Recrystallization by dissolving in 50 ml of benzene and diluting with hexane gives 5.5 g of white crystals, mp 106°–107° C.

EXAMPLE 11

2-(4'-tert.-Butylphenoxy)ethanol-O-methanesulfonate

To a solution of 19.4 go of 2-(4'-tert.-butylphenoxy)ethanol and 20.7 ml of triethylamine in 250 ml of dichloromethane chilled to −10° C. is added dropwise a solution of 8.5 ml of methanesulfonyl chloride in 20 ml of dichloromethane. The mixture is stirred for 1 hour and then washed with 200 ml portions of ice-water, 1N hydrochloric acid, saturated sodium bicarbonate and saturated sodium chloride solutions. The dichloromethane layer is dried (MgSO$_4$) and the solvent removed under reduced pressure to give the product as an oil.

EXAMPLE 12

Methyl{p-[(2-(p-tert.-butylphenoxy)ethoxy]phenyl}acetate

To a 4.0 g portion of a 60% sodium hydride-oil dispersion under argon is added hexane and the hexane removed. To the sodium hydride freed of oil is added 100 ml of N,N-dimethylacetamide and a solution of 16.6 g of methyl(p-hydroxyphenyl)acetate in 40 ml of N,N-dimethylacetamide. The mixture is stirred for 90 minutes and a solution of 2-(4'-tert-butylphenoxy)ethanol O-methanesulfonate in 30 ml of N,N-dimethylacetamide is added. The mixture is stirred and heated at 100° C. for 18 hours and poured into 1 liter of ice-water containing 5 ml of acetic acid. The mixture is filtered and the solid washed with water to give 29.9 g of product as crystals. Recrystallization from 600 ml of methanol gives 22.4 g of gray crystals, mp 113°–115° C.

EXAMPLE 13

Methyl bromo{p-[2-(p-tert.-butylphenoxy)ethoxy]phenyl}acetate

A mixture of 11.4 g of methyl{p-[2-(p-tert.-butylphenoxy)ethoxy]phenyl}acetate and 5.6 g of N-bromosuccinimide in 150 ml of carbon tetrachloride is refluxed for 24 hours or until the reaction is complete. The mixture is cooled and filtered through a column of silica gel with dichloromethane as eluent to give 12 g of a gum. Trituration with petroleum ether containing a small amount of ether gives 10.4 g of white crystals, mp 41°–45° C.

EXAMPLE 14

Methyl(p-chlorophenoxy){p-[2-(p-tert.-butylphenoxy)ethoxy]phenyl}acetate

A mixture of 1.55 g of p-chlorophenol, 0.47 g of 60% sodium hydride-oil dispersion and 20 ml of tetrahydrofuran is stirred at room temperature for 90 minutes. To the mixture is added 2.22 g of potassium iodide, 1 ml of hexamethylphosphoramide and dropwise 5.04 g of methyl bromo{p-[2-(p-tert.-butylphenoxy)ethoxy]phenyl}acetate in 30 ml of tetrahydrofuran. The mixture is refluxed for 18 hours and poured into 350 ml of ice-water containing 1 ml of acetic acid. After stirring in an ice bath for 30 minutes, the mixture is filtered and the solid washed with water to give 5.5 g of product as tan crystals. Recrystallization by dissolving in acetone, adding hexane and distilling off the acetone gives 3.9 g of white crystals, mp 128°–130° C.

EXAMPLE 15

Methyl(p-tert.-butylphenoxy){p-[2-(p-tert.-butylphenoxy)ethoxy]phenyl}acetate

A mixture of 2.77 g of tert.-butylphenol and 0.73 g of 60% sodium hydride-oil dispersion in 40 ml of tetrahydrofuran is stirred at room temperature for 1 hour. To the mixture is added 3.07 g of potassium iodide, 1.5 ml of hexamethylphosphoramide and dropwise 7.78 g of methyl bromo{p-[2-(p-chlorophenoxy)ethoxy]phenyl}acetate in 30 ml of tetrahydrofuran. The mixture is refluxed for 18 hours and poured into 500 ml of ice-water containing 1.5 ml of acetic acid. After stirring in the ice bath, the mixture is filtered to give 8.7 g of gummy solid. The solid is crystallized from hexane to give 6.3 g of off-white crystals. Recrystallization from hexane gives 5.2 g of white crystals, mp 50° C. partially melts, resolidifies ca 70° C. and gives clear melt at 90° C.

EXAMPLE 16

2-(p-chlorophenoxy)ethanol O-methanesulfonate

To a solution of 61.3 g of 2-(p-chlorophenoxy)ethanol, 73.5 ml of triethylamine and 900 ml of dichloromethane chilled at −10° C. is added dropwise a solution of 30.2 ml of methanesulfonyl chloride in 60 ml of dichloromethane. The mixture is stirred at −8° C. for 1 hour and worked up as described in Example 11 to give the product as a white solid. A dried sample of product melted at 75°-77° C.

EXAMPLE 17

Methyl{p-[2-(p-chlorophenoxy)ethoxy]phenyl}acetate

A 14.4 g sample of 60% sodium hydride-oil dispersion is washed with hexane to remove the oil. To the sodium hydride is added 300 ml of N,N-dimethylacetamide and dropwise a solution of 58.5 g of methyl(p-hydroxyphenyl)acetate in 100 ml of N,N-dimethylacetamide. The mixture is stirred at room temperature for 1 hour and then at 50° C. for 30 minutes and a solution of 2-(p-chlorophenoxy)ethanol O-methanesulfonate (0.35 mole) in 150 ml of N,N-dimethylacetamide is added. The mixture is heated at 100° C. for 18 hours and poured into 2.5 liters of ice-water containing 50 ml of acetic acid. The mixture is filtered and the solid washed with water to give 114.6 g of solid. A 10 g sample is crystallized twice from methanol to give 5.7 g of white crystals, mp 93°-95° C.

EXAMPLE 18

Methyl bromo{p-[2-(p-chlorophenoxy)ethoxy]phenyl}acetate

A mixture of 64 g of methyl{p-[2-(p-chlorophenoxy)ethoxy]phenyl}acetate and 37.4 g of N-bromosuccinimide in 800 ml of carbon tetrachloride is stirred and refluxed for 72 hours or until the reaction is complete. The solution is filtered and the filtrate passed through a silica gel column with carbon tetrachloride as eluent to give 49.4 g of white crystals, mp 76°-80° C.

EXAMPLE 19

Methyl(p-chlorophenoxy){p-[2-(p-chlorophenoxy)ethoxy]phenyl}acetate

As described in Example 5, a mixture of 2.52 g of p-chlorophenol, 0.785 g of 60% sodium hydride-oil dispersion, 3.60 g of potassium iodide and 7.8 g of methyl bromo{p-[2-(p-chlorophenoxy)ethoxy]phenyl}acetate in 70 ml of tetrahydrofuran are refluxed for 18 hours and worked up to give 8.6 g of oil. The oil is triturated with hexane to give 6.9 g of tan crystals. Two recrystallizations from methanol gives the product as white crystals, mp 97°-112° C.

EXAMPLE 20

Methyl(m-dimethylaminophenoxy){p-[2-(p-chlorophenoxy)ethoxy]phenyl}acetate

As described in Example 5, a mixture of 2.74 g of 3-dimethylaminophenol, 0.80 g of 60% sodium hydride-oil dispersion, 3.32 g of potassium iodide, one ml of hexamethylphosphoramide and 8.0 g of methyl bromo{p-[2-(p-chlorophenoxy)ethoxy]phenyl}acetate in 70 ml of tetrahydrofuran is refluxed for 18 hours and worked up to give 8.34 g of a gum. The gum is chromatographed on silica gel with dichloromethane as eluent to give 6.8 g of solid. Trituration with hexane-ether gives 3.50 g of crystals. Recrystallization gives crystals, mp 100°-101° C.

EXAMPLE 21

Methyl(5-indanyloxy){p-[2-(p-tert.-butylphenoxy)ethoxy]phenyl}acetate

As described in Example 5, a mixture of 1.61 g of 5-indanol, 0.47 g of 60% sodium hydride-oil dispersion, 2.22 g of potassium iodide, 1 ml of hexamethylphosphoramide and 5.04 g of methyl bromo{p-[2-(p-tert.-butylphenoxy)ethoxy]phenyl}acetate in 50 ml of tetrahydrofuran is refluxed and worked up to give 6.4 g of gum. Trituration with petroleum ether containing a small amount of ether gives 4.3 g of tan crystals. Recrystallization from hexane-acetone gives crystals, mp 149°-151° C.

EXAMPLE 22

[p-(3-Chloropropoxy)phenyl]acetic acid

To a solution of 41 g of potassium hydroxide in 250 ml of ethanol is added 50 g of p-hydroxyphenylacetic acid. To this solution is added 32 ml of 3-bromo-1-chloropropane and the mixture is refluxed for 4 hours. The mixture is cooled in an ice bath and filtered. The filtrate is acidified to pH 2 with concentrated HCl. Filtration gives a solid which is washed with water to give 68 g of product. Recrystallization from acetic acid water gives white crystals, mp 89°-91° C.

EXAMPLE 23

{p-[3-(p-Chlorophenoxy)propoxy]phenyl}acetic acid

To a solution of 2.58 g of p-chlorophenol in 25 ml of ethanol is added 2.64 g of 85% potassium hydroxide solution, 3.6 g of potassium iodide and 4.6 g of [p-(3-chloropropoxy)phenyl]acetic acid. The mixture is refluxed for 18 hours, diluted with water, acidified with concentrated HCl and filtered to give 4.74 g of crystals. Recrystallization from acetic acid-water gives 3.85 g of white crystals, mp slowly melts 131°-150° C.

EXAMPLE 24

Methyl{p-[3-(p-chlorophenoxy)propoxy]phenyl}acetate

A solution of 15.0 g of {p-[3-(p-chlorophenoxy)propoxy]phenyl}acetic acid in 35 ml of thionyl chloride is heated on a steam bath for 1 hour. The thionyl chloride is removed under reduced pressure and the residue dissolved in 100 ml. of benzene and 20 ml. of methanol. After stirring for 20 minutes, the solution is washed with sodium chloride solution, saturated sodium bicarbonate solution and dried (MgSO$_4$). Removal of the solvent under reduced pressure gives 15.4 g of colorless oil.

EXAMPLE 25 p-Chlorophenyl 3-chloropropyl ether

A mixture of 157 g of 3-bromo-1-chloropropane, 129 g of p-chlorophenol and 165 g of potassium carbonate in 1 liter of acetone is refluxed for 3 days. The mixture is cooled, filtered and the filtrate concentrated under reduced pressure. The residue is distilled to give 184 g of product as an oil, bp 107°-116° C. at 0.5mm.

EXAMPLE 26

Methyl{p-[3-(p-chlorophenoxy)propoxy]acetate

A 24.8 g sample of 60% sodium hydride-oil dispersion is washed twice with hexane under argon and then 600 ml of N,N-dimethylacetamide is added. To the mixture is added dropwise 104 g of methyl p-hydroxyphenylacetate in 240 ml of N,N-dimethylacetamide. The mixture is stirred at room temperature for 1 hour and at 50° C. for 30 minutes. To the mixture is added 103 g of potassium iodide, 30 ml of hexamethylphosphoramide and dropwise 127 g of p-chlorophenyl 3-chloropropyl ether in 180 ml of N,N-dimethylacetamide. The mixture is heated at 100° C. (oil bath) for 18 hours and poured into 5 liters of ice-water containing 30 ml of acetic acid. The mixture is stirred in an ice bath until the oil, which separates, solidifies. The mixture is filtered and the solid washed with water. The damp solid is dissolved in 600 ml of methanol, treated with activated carbon and the mixture filtered. The filtrate is chilled and filtered to give 108 g of white crystals. Recrystallization from methanol gives white crystals, mp 45°–49° C.

EXAMPLE 27

Methyl[p-(3-chloropropoxy)phenyl]acetate

A mixture of 47.4 g of methyl p-hydroxyphenylacetate, 28.5 ml of 3-bromo-1-chloropropane, 38.6 g of potassium carbonate and 700 ml of acetone is stirred and refluxed for 24 hours. The mixture is chilled, filtered and the solvent removed under reduced pressure. Distillation of the residue gives 52.1 g of colorless oil, bp 144°–146° C. at 0.25mm.

EXAMPLE 28

Methyl{p-[3-(p-chlorophenoxy)propoxy]phenyl}acetate

An 8.75 g sample of 60% sodium hydride-oil dispersion is washed with hexane under argon. To the hydride is added 200 ml of N,N-dimethylacetamide and dropwise is added 26.4 g of p-chlorophenol in 80 ml of N,N-dimethylacetamide. The mixture is stirred at room temperature for 90 minutes and 34.2 g of potassium iodide and 10 ml of hexamethylphosphoramide is added. To the mixture is added a solution of 52.1 g of methyl[p-(3-chloropropoxy)phenyl]acetate in 60 ml of N,N-dimethylacetamide and the mixture is heated at 100° C. for 18 hours. The mixture is cooled and poured into 1.1 liters of ice-water containing 10 ml of acetic acid. The mixture is stirred in an ice bath until the oil that separates solidifies. The mixture is filtered and the solid washed with water to give 65 g of gummy solid. The solid is slurried in 300 ml of methanol, the mixture is filtered and the filtrate concentrated under reduced pressure to give the product as an oil.

EXAMPLE 29

Methyl bromo{p-[3-(p-chlorophenoxy)propoxy]phenyl}acetate

A mixture of 33.5 g of methyl{p-[3-(p-chlorophenoxy)propoxy]phenyl}acetate and 19.6 g of N-bromosuccinimide in 400 ml of carbon tetrachloride is refluxed for 24 hours or until the reaction is complete. The mixture is cooled, filtered and the filtrate passed through a column of silica gel with carbon tetrachloride as eluent to give 27.2 g of product as an oil. Crystallization from petroleum ether gives white crystals, mp 49°–53° C.

EXAMPLE 30

Methyl(p-chlorophenoxy){p-[3-(p-chlorophenoxy)propoxy]phenyl}acetate

A mixture of 2.57 g of p-chlorophenol, 0.72 g of 60% sodium hydride-oil dispersion and 25 ml of tetrahydrofuran is stirred at room temperature for 90 minutes. To the mixture under argon is added 3.32 g of potassium iodide, 1 ml of hexamethylphosphoramide, and dropwise a solution of 7.5 g of methyl bromo{p-[3-(p-chlorophenoxy)propoxy]phenyl}acetate. The mixture is stirred at room temperature for 1 hour and refluxed for 18 hours. The mixture is poured into 500 ml of ice-water containing 1.2 ml of acetic acid. The mixture is extracted with ether and the extracts washed with saturated sodium chloride solution and dried (MgSO₄). The solvent is removed under reduced pressure to give 8.0 g of product as an oil. Chilling gives crystals. Recrystallization from 90% ethanol gives white crystals, mp 80°–82° C.

EXAMPLE 31

Methyl(p-tert.-butylphenoxy){p-[3-(p-chlorphenoxy)propoxy]phenyl}acetate

As described in Example 30, a mixture of 3.13 g of p-tert.-butylphenol, 0.755 g of 60% sodium hydride-oil dispersion, 3.5 g of potassium iodide, one ml of hexamethylphosphoramide and 7.9 g of methyl bromo{p-[3-(p-chlorophenoxy)propoxy]phenyl}acetate in 70 ml of tetrahydrofuran is refluxed for 18 hours and worked-up to give 9.0 g of an oil. The oil is chromatographed over silica gel with dichloromethane as eluent to give 7.4 g of oil which is crystallized from petroleum ether-ether to give 5.7 g of white crystals, mp 98°–101° C.

EXAMPLE 32

Methyl($\alpha,\alpha,\alpha$-trifluoro-m-tolyloxy){p-[3-(p-chlorophenoxy)propoxy]phenyl}acetate As described in Example 30, a mixture of 3.4 g of m-trifluoromethylphenol, 0.755 g of 60% sodium hydride-oil dispersion, 3.5 g of potassium iodide, one ml of hexamethylphosphoramide and 7.9 g of methyl bromo{p-[3-(p-chlorophenoxy)propoxy]phenyl}acetate in 70 ml of tetrahydrofuran is refluxed for 18 hours and worked-up to give 10 g of oil. Purification gives 8.6 g of light amber oil.

EXAMPLE 33

($\alpha,\alpha,\alpha$-Trifluoro-m-tolyloxy){p-[3-(chlorophenoxy)propoxy]phenyl}acetic acid diisopropylamine salt A mixture of 8.6 g of potassium hydroxide, 8.6 g of methyl($\alpha,\alpha,\alpha$-trifluoro-m-tolyloxy){p-[3-(p-chlorophenoxy)propoxy]phenyl}acetate, 150 ml of water and 20 ml of ethanol is refluxed for 5 hours. The hot mixture is acidified with HCl and the mixture is extracted with ether. The ether extract is washed with saturated sodium chloride solution, dried (MgSO₄) and the solvent removed under reduced pressure to give 5.5 g of product as a gum. A 6.3 g portion of gum, prepared as described above, is dissolved in ether. Diisopropylamine and hexane are added and the mixture is chilled to give 5.92 g of yellow crystals. Recrystallization from methanol-water gives 5.3 g of product as pale yellow crystals, mp 124°–126° C.

EXAMPLE 34

Methyl(m-phenoxyphenoxy){p-[3-(p-chlorophenoxy)-propoxy]phenyl}acetate

As described in Example 30, a mixture of 5.2 g of m-phenoxyphenol, 1.06 g of 60% sodium hydride-oil dispersion, 3.82 g of potassium iodide, one ml of hexamethylphosphoramide and 10.4 g of methyl bromo{p-[3-(p-chlorophenoxy)propoxy]phenyl}acetate in 80 ml of tetrahydrofuran is refluxed for 18 hours and worked-up to give 13.6 g of gum. The gum is chromatographed over silica gel with dichloromethane as eluent to give 11.2 g of product as a viscous oil.

EXAMPLE 35

Methyl(p-phenoxyphenoxy){p-[3-(p-chlorophenoxy)-propoxy]phenyl}acetate

To a mixture of 4.66 g of p-phenoxyphenol, 1.19 g of sodium methoxide, 10 ml of benzene and 40 ml of methanol is added 8.27 g of methyl bromo{p-[3-(p-chlorophenoxy)propoxy]phenyl}acetate in 10 ml of benzene. The mixture is refluxed for 22 hours and the solvent removed under reduced pressure. The residue is chromatographed over silica gel with dichloromethane as eluent giving a viscous oil which is again chromatographed over silica gel with dichloromethane as eluent. There is obtained 4.3 g of viscous oil which is crystallized from methylcyclohexane-methanol to give 3.6 g of white crystals, mp 78°–80° C.

EXAMPLE 36

Methyl(4-chloro-3-methylphenoxy){p-[3-(p-chlorophenoxy)propoxy]phenyl}acetate

As described in Example 30, a mixture of 2.86 g of 4-chloro-3-methylphenol, 0.80 g of 60% sodium hydride-oil dispersion, 3.32 g of potassium iodide, one ml of hexamethylphosphoramide and 8.52 g of methyl bromo{p-[3-(p-chlorophenoxy)propoxy]phenyl}acetate in 70 ml of tetrahydrofuran is refluxed for 18 hours and worked-up to give 10.1 g of gum. The gum is crystallized from petroleum ether containing a small amount of ether to give 7.7 g of white crystals. Purification by chromatography over silica gel with dichloromethane and recrystallization from petroleum ether-ether and benzene-hexane gives crystals, mp 74°–76° C.

EXAMPLE 37

Methyl(5-indanyloxy){p-[3-(p-chlorophenoxy)propoxy]phenyl}acetate

As described in Example 30, a mixture of 2.68 g of 5-indanol, 0.80 g of 60% sodium hydride-oil dispersion, 3.33 g of potassium iodide, 1 ml of hexamethylphosphoramide and 8.25 g of methyl bromo{p-[3-(p-chlorophenoxy)propoxy]phenyl}acetate in 65 ml of tetrahydrofuran is refluxed for 18 hours and worked-up to give 8.7 g of gum. The gum is dissolved in 50 ml of benzene and 200 ml of hexane is added. Chilling gives 2.95 g of crystals, mp 60°–62° C.

EXAMPLE 38

(5-Indanyloxy){p-[3-(p-chlorophenoxy)propoxy]phenyl}acetic acid

A mixture of 5 g of potassium hydroxide, 7.0 g of methyl(5-indanyloxy){p-[3-(p-chlorophenoxy)propoxy]phenyl}acetate, 5 ml of methanol and 50 ml of water is refluxed for 4 hours. The mixture is acidified with concentrated HCl, chilled and the aqueous layer decanted from the gum which separated. The gum is washed with water, dissolved in chloroform and the solution dried (MgSO$_4$). The solvent is removed under reduced pressure to give 6.8 g of gum. The gum is crystallized from petroleum ether containing a small amount of ether to give 5.4 g of off-white crystals. Recrystallization from chloroform-hexane gives white crystals, mp 104°–108° C.

EXAMPLE 39

Methyl(p-benzyloxyphenoxy){p-[3-(p-chlorophenoxy)propoxy]phenyl}acetate

To a mixture of 8.27 g of methyl bromo{p-[3-(p-chlorophenoxy)propoxy]phenyl}acetate, 5.0 g of p-benzyloxyphenol, 50 mg of potassium iodide, 10 ml of benzene and 40 ml of methanol is added 1.19 g of sodium methoxide. The mixture is refluxed for 24 hours and the solvent removed under reduced pressure. To the residue is added acetone and hexane and the solids filtered off. The filtrate is dried (MgSO$_4$) and the solvent removed under reduced pressure. The residue is chromatographed over silica gel with dichloromethane as eluent. The oil obtained is crystallized from hexane-methanol to give 5.6 g of crystals. Recrystallization from methanol-ethyl acetate gives crystals, mp 98°–101° C.

EXAMPLE 40

(p-Benzyloxyphenoxy){p-[3-(p-chlorophenoxy)propoxy]phenyl}aceticacid

A mixture of 4.5 g of methyl(p-benzyloxyphenoxy){p-[3-(p-chlorophenoxy)propoxy]phenyl}acetic acid, 5.5 g of potassium hydroxide, 3 ml of water and 150 ml of ethanol is refluxed for 4 hours. The mixture is acidified with concentrated HCl and extracted with chloroform. The extract is dried (MgSO$_4$) and the solvent removed under reduced pressure. The oil is dissolved in benzene and the solution diluted with hexane. On standing, crystals separate and are filtered off and recrystallized from benzene-hexane to give 2.15 g of light tan crystals, mp 105°–109° C.

EXAMPLE 41

Methyl(p-cyanophenoxy){p-[3-(p-chlorophenoxy)-propoxy]phenyl}acetate

To a mixture of 2.98 g of p-cyanophenol and 40 ml of methanol is added 1.19 g of sodium methoxide. To the mixture is added 8.22 g of methyl bromo{p-[3-(p-chlorophenoxy)propoxy]phenyl}acetate and 10 ml of benzene. The mixture is refluxed for 22 hours and the solvent removed under reduced pressure. The residue is chromatographed over silica gel with dichloromethane as the solvent. The product is obtained as an oil which is crystallized from methylcyclohexane-methanol and a small amount of hexane. Crystals are obtained and washed with hexane-methanol to give 3.7 g of white crystals, mp 102°–104° C.

EXAMPLE 42

Methyl(m-tert.-butylphenoxy){p-[3-(p-chlorophenoxy)propoxy]phenyl}acetate

To a mixture of 8.27 g of methyl bromo{p-[3-(p-chlorophenoxy)propoxy]phenyl}acetate, 3.75 g of m-tert.-butylphenol, 10 ml of benzene and 40 ml of methanol is added 1.19 g of sodium methoxide and 50 mg of potassium iodide. The mixture is refluxed for 24 hours and the solvent removed under reduced pressure. To the residue is added acetone and hexane and the mixture is filtered. The filtrate is dried (MgSO$_4$) and concentrated under reduced pressure to give an oil. The oil is chromatographed over silica gel with dichloromethane as eluent to give 4.72 g of product as a colorless viscous oil.

EXAMPLE 43

Methyl(3,4-dimethylphenoxy){p-[3-(p-chlorophenoxy)-propoxy]phenyl}acetate

To a mixture of 3.05 g of 3,4-dimethylphenol, 1.19 g of sodium methoxide, 40 ml of methanol and 10 ml of benzene is added 8.27 g of methyl bromo{p-[3-(p-chlorophenoxy)propoxy]phenyl}acetate. The mixture is refluxed for 24 hours and the solvent removed under reduced pressure. The residue is chromatographed over silica gel with dichloromethane as eluent. The product is obtained as a viscous oil.

EXAMPLE 44

Methyl(2-chloro-4-tert.-butylphenoxy){p-[3-(p-chlorophenoxy)propoxy]phenyl}acetate A mixture of 4.25 g of 4-tert.-butyl-2-chlorophenol, 30 ml of tetrahydrofuran and 0.88 g of sodium hydride (60% dispersion in oil) is stirred at room temperature for 1 hour. To the mixture is added 3.48 g of potassium iodide and then a solution of 8.28 g of methyl bromo{p-[3-(p-chlorophenoxy)propoxy]phenyl}acetate in 30 ml of tetrahydrofuran is added dropwise. After stirring and heating in an oil bath at 60° C. for 18 hours, the mixture is poured into ice-water containing 3 ml of acetic acid. The mixture is extracted with ethyl acetate and the combined extracts washed with sodium bicarbonate solution, 10% sodium bisulfite and saturated sodium chloride solution. The dried (MgSO$_4$) extract is concentrated under reduced pressure to give an amber gum. The gum is dissolved in dichloromethane and the solution passed through a column of silica gel with dichloromethane as eluent. From the main cuts there is obtained 10 g of product as a viscous oil.

EXAMPLE 45

(2-Chloro-4-tert.-butylphenoxy){p-[3-(p-chlorophenoxy)propoxy]phenyl}acetic acid, diisopropylamine salt A mixture of 10 g of methyl(2-chloro-4-tert.-butylphenoxy){p-[3-(p-chlorophenoxy)propoxy]phenyl}acetate, 50 ml of ethanol, 6 g of KOH and 50 ml of water is refluxed for 4 hours. The mixture is acidified while hot with concentrated HCl, chilled and diluted with water. The mixture is extracted with dichloromethane and the extract dried (MgSO$_4$) and concentrated under reduced pressure to give 9.6 g of a gum. The gum is dissolved in 50 ml of ether and 4.9 ml of diisopropylamine is added. Hexane is added. Chilling gives crystals which are filtered off to give 8.56 g of product. Washing with acetone, ether, and finally hexane gives 7.3 g of white crystals, mp 173°–176° C.

EXAMPLE 46

Methyl(m-chlorophenoxy){p-[3-(p-chlorophenoxy)-propoxy]phenyl}acetate

As described in Example 44, 8.28 g of methyl bromo{p-[3-(p-chlorophenoxy)propoxy]phenyl}acetate is reacted with 2.96 g of m-chlorophenol to give 8.8 g of the product as a viscous oil.

EXAMPLE 47

(m-Chlorophenoxy){p-[3-(p-chlorophenoxy)propoxy]-phenyl}acetic acid, diisopropylamine salt An 8.8 g portion of methyl(m-chlorophenoxy){p-[3-(p-chlorophenoxy)propoxy]phenyl}acetate is hydrolysed as described in Example 45 to give 7.5 g of a gum. The gum in 50 ml of ether, 4.5 ml of diisopropylamine and 40 ml of hexane gives 7.61 g of product as white crystals. Recrystallization from methanol gives 3.6 g of white crystals, mp 149°–151° C.

EXAMPLE 48

Methyl(5,6,7,8-tetrahydro-2-naphthyloxy){p-[3-(p-chlorophenoxy)propoxy]phenyl}acetate As described in Example 44, 8.28 g of methyl bromo{p-[3-(p-chlorophenoxy)propoxy]phenyl}acetate is reacted with 3.4 g of 5,6,7,8-tetrahydro-2-naphthol to give 9.2 g of product as a viscous oil.

EXAMPLE 49

(5,6,7,8-Tetrahydro-2-naphthyloxy){p-[3-(p-chlorophenoxy)propoxy]phenyl}acetic acid, diisopropylamine salt A 9.2 g of portion of methyl(5,6,7,8-tetrahydro-2-naphthyloxy){p-[3-(p-chlorophenoxy)propoxy]phenyl}acetate is hydrolysed as described in Example 45 to give 8.2 g of a gum. The gum is dissolved in ether, diisopropylamine and hexane is added to give 6 g of product as white crystals, mp 123°–126° C.

EXAMPLE 50

Methyl(p-cyclohexylphenoxy){p-[3-(p-chlorophenoxy)propoxy]phenyl}acetate

As described in Example 44, 8.72 g of methyl bromo{p-[3-(p-chlorophenoxy)propoxy]phenyl}acetate is reacted with 4.05 g of p-cyclohexylphenol to give 8.81 g of product as off-white crystals. Recrystallization from methanol gives white crystals, mp 93°–95° C.

EXAMPLE 51

Methyl(α,α,α-trifluoro-p-tolyloxy){p-[3-(p-chlorophenoxy)propoxy]phenyl}acetate

As described in Example 44, 8.14 g of methyl bromo{p-[3-(p-chlorophenoxy)propoxy]phenyl}acetate is reacted with p-trifluoromethylphenol to give 7.7 g of off-white crystals. Recrystallization from methanol gives the product as white crystals, mp 83°–84° C.

EXAMPLE 52

Methyl(p-cyclohexylphenoxy){p-[2-(p-chlorophenoxy)ethoxy]phenyl}acetate

As described in Example 44, 8.0 g of methyl bromo{p-[2-(p-chlorophenoxy)ethoxy]phenyl}acetate is reacted with 4.05 g of p-cyclohexylphenol to give 8.6 g of product as tan crystals. Recrystallization from methanol gives off-white crystals, mp 108°–110° C.

EXAMPLE 53

Methyl(α,α,α-trifluoro-p-tolyloxy){p-[2-(p-chlorophenoxy)ethoxy]phenyl}acetate

As described in Example 44, 8.0 g of methyl bromo{p-[2-(p-chlorophenoxy)ethoxy]phenyl}acetate is reacted with p-trifluoromethylphenol to give 7.4 g of product as white crystals. Recrystallization from methanol gives white crystals, mp 95°–97° C.

EXAMPLE 54

(α,α,α-Trifluoro-m-tolyloxy){p-[(p-chlorophenoxy)methoxy]phenyl}acetic acid diisopropylamine salt To a solution of 4.05 g of m-trifluoromethylphenol, 40 ml of methanol and 1.19 g of sodium methoxide is added 7.71 g of methyl bromo{p-[(p-chlorophenoxy)methoxy]phenyl}acetate in 10 ml of benzene. The mixture is refluxed for 21 hours and the solvent removed under reduced pressure. The residue is triturated with dichloromethane, filtered and the filtrate chromatographed on a column of silica gel (eluent methylene chloride). The main fraction is collected and the solvent removed under reduced pressure to give an oil. The above oil is combined with 4.0 g of potassium hydroxide, 75 ml of ethanol:water (9:1) and the mixture is refluxed for 4 hours. The mixture is concentrated under reduced pressure, diluted with water and acidified with concentrated HCl. The mixture is extracted with dichloromethane, the extract is dried (MgSO$_4$) and the solvent removed under reduced pressure to give an oil. The above oil is dissolved in ether, diisopropylamine is added and the solution is diluted with hexane. Chilling and filtering gives 6.75 g of product as off-white crystals, mp 95°–100° C.

EXAMPLE 55

3-(p-Chlorophenoxy)propan-2-ol

A mixture of 5.16 g of p-chlorophenol, 50 ml of methanol and 0.40 g of sodium hydride (60% dispersion in oil) is stirred for 1 hour. To the solution is added dropwise a solution of 3.0 ml of propylene oxide in 10 ml of methanol. The mixture is stirred and refluxed overnight and the solvent removed under reduced pressure. The residual oil is dissolved in carbon tetrachloride, washed with water and dried (MgSO$_4$) to give 6.7 g of product as an oil.

In a similar run with 67 g of p-chlorophenol and 70 ml of propylene oxide, there is obtained 83.6 g of oil which is distilled to give 78.1 g of clear oil, bp 117°–125° C. at 0.5mm.

EXAMPLE 56

3-(p-Chlorophenoxy)propan-2-ol O-methanesulfonate

To a solution of 37.4 g of 3-(p-chlorophenoxy)propan-2-ol and 41 ml of triethylamine in 500 ml of dichloromethane stirred and chilled at −8° C. is added dropwise 18.7 ml of methanesulfonyl chloride in 50 ml of dichloromethane. After stirring at −8° C. for 1 hour, the solution is washed with 350 ml portions of ice cold water, 1N HCl, saturated NaCl, saturated NaHCO$_3$ and saturated NaCl. The organic layer is dried (MgSO$_4$) and the solvent removed under reduced pressure to give 54 g of product as white crystals, mp 72°–78° C.

EXAMPLE 57

Methyl{p-[2-(p-chlorophenoxy)-1-methylethoxy]phenyl}acetate

To a suspension of 8.0 g of sodium hydride (60% dispersion in oil) (washed with hexane) in 190 ml of N,N-dimethylacetamide is added dropwise 35.2 g of methyl p-hydroxyphenylacetate in 60 ml of N,N-dimethylacetamide. The mixture is stirred at room temperature for one hour and at 50° C. for 20 minutes. To the mixture is added dropwise 53 g of 3-(p-chlorophenoxy)propan-2-ol O-methanesulfonate in 100 ml of N,N-dimethylacetamide. The mixture is stirred and heated at 100° C. for 18 hours. After pouring into 2 liters of ice-water containing 6 ml of acetic acid and chilling in an ice bath for 2 hours, the mixture is filtered and the solid washed with water. The damp waxy product is dissolved in dichloromethane and the solution dried (MgSO$_4$). The solvent is removed under reduced pressure to give 52.6 g of product as an oil. The oil is crystallized from hexane and recrystallized from methanol to give the product as white crystals, mp 84°–85° C.

EXAMPLE 58

Methyl bromo{p-[2-(p-chlorophenoxy)-1-methylethoxy]phenyl}acetate

A mixture of 10.0 g of methyl{p-[2-(p-chlorophenoxy)-1-methylethoxy]phenyl}acetate, 5.87 g of N-bromosuccinimide and 120 ml of carbon tetrachloride is stirred and refluxed for 5 days. The mixture is cooled, filtered and the filtrate is passed through a short column of silica gel (125 ml cuts). The first two cuts are combined and the solvent removed to give 12.0 g of colorless gum.

EXAMPLE 59

Methyl(p-tert.-butylphenoxy){p-[2-(p-chlorophenoxy)-1-methylethoxy]phenyl}acetate To a solution of 2.36 g of p-t-butylphenol in 3 ml of tetrahydrofuran is added 0.625 g of sodium hydride (60% dispersion in oil). After stirring under argon for 1 hour and heating at 50° C. for 20 minutes, 2.4 g of potassium iodide and 6.0 g of methyl bromo{p-[2-(p-chlorophenoxy)-1-methylethoxy]phenyl}acetate in 30 ml of tetrahydrofuran is added. The mixture is stirred and refluxed for 18 hours and poured into 300 ml of ice-water containing 3 ml of acetic acid. The mixture is extracted with dichloromethane and the extracts washed with saturated NaHCO$_3$, 10% sodium thiosulfate and saturated sodium chloride solution. The dichloromethane extract is dried (MgSO$_4$) and the solvent removed under reduced pressure to give 6.7 g of product as a gum. Chromatography over silica gel with dichloromethane as eluent gives 5.7 g of yellow gum.

EXAMPLE 60

(p-tert.-Butylphenoxy){p-[2-(p-chlorophenoxy)-1-methylethoxy]phenyl}acetic acid

A 5.7 g sample of methyl(p-tert.-butylphenoxy){p-[2-(p-chlorophenoxy)-1-methylethoxy]phenyl}acetate is hydrolyzed as described in Example 45 to give 4.9 g of gum. The gum is crystallized from hexane-ether to give 4.0 g of pale yellow crystals, 100°–107° C.

EXAMPLE 61

Methyl(α,α,α-trifluoro-p-tolyoxy){p-[2-(p-chlorophenoxy)-1-methylethoxy]phenyl}acetate As described in Example 59, 6.0 g of methyl bromo{p-[2-(p-chlorophenoxy)-1-methylethoxy]phenyl}acetate is reacted with 2.54 g of p-trifluoromethylphenol to give 5.7 g of product as a gum.

EXAMPLE 62

(α,α,α-Trifluoro-p-tolyoxy){p-[2-(p-chlorophenoxy)-1-methylethoxy]phenyl}acetic acid A 5.7 g sample of methyl(α,α,α-trifluoro-p-tolyoxy){p-[2-(p-chlorophenoxy)-1-methylethoxy]phenyl}acetate is hydrolyzed as described in Example 45 to give 5.1 g of yellow gum. Crystallization from hexane-ether gives 4.42 g of yellow crystals, mp 115°–119° C.

EXAMPLE 63

Methyl 2-(p-tert.-butylphenoxy)-2-{p-[3-(p-chlorophenoxy)propoxy]phenyl}propionate A solution of 2.7 ml of N,N-diisopropylamine in 15 ml of tetrahydrofuran under argon is stirred and cooled to 0° C. To the solution is added dropwise 8.5 ml of 2M n-butyllithium in hexane. The solution is cooled to −70° C. and a solution of 7.24 g of methyl(p-tert.-butylphenoxy){p-[3-(p-chlorophenoxy)propoxy]phenyl}acetate in 15 ml of tetrahydrofuran is added dropwise. After stirring at −70° C. for 30 minutes, 1.87 ml of methyl iodide is added and the mixture is stirred while slowly allowing to warm to room temperature. The mixture is poured into 100 ml of water and is extracted with ether. The ether extract is washed with 10% HCl, water, saturated NaCl and dried (MgSO$_4$). The solvent is removed under reduced pressure to give 7.5 g of a clear gum. Chromatography over silica gel with dichloromethane-hexane as eluent gives 5.6 g of colorless gum.

EXAMPLE 64

Methyl 2-(p-tert.-butylphenoxy)-2-{p-[3-(p-chlorophenoxy)propoxy]phenyl}octanoate As described in Example 63, 7.24 g of methyl (p-tert.-butylphenoxy) {p-[3-(p-chlorophenoxy)propoxy]phenyl}acetate is reacted with 6.36 g of n-hexyl iodide to give the product as a tan oil. The oil is chromatographed over silica gel with hexane as eluent (125 ml cuts) and then methylene chloride:- hexane (1:1) as eluent. Cuts 6–8 give 6.0 g of product as an oil.

EXAMPLE 65

3-(p-Chlorophenoxy)propan-2-ol

To a solution of 3.87 g of p-chlorophenol in 30 ml of tetrahydrofuran is added 1.2 g of sodium hydride (60% dispersion in oil). After one hour, 4.98 g of potassium iodide and 2.54 ml of 1-chloro-2-propanol in 10 ml of tetrahydrofuran is added. The mixture is heated at 80° C. for 18 hours. The mixture is chilled, poured into 300 ml of ice-water containing 3 ml of acetic acid. The mixture is extracted with dichloromethane and the extract washed with saturated sodium bicarbonate and sodium chloride solution. Drying (MgSO$_4$) and removal of the solvent under reduced pressure gives 5.1 g of product as an oil.

EXAMPLE 66 p-Chloro-β-methylphenethyl alcohol

To 833 ml. of a chilled solution (0° C.) of 1M diborane in tetrahydrofuran is added dropwise a solution of 96 g. of 2-(p-chlorophenoxy)propionic acid in 500 ml. of tetrahydrofuran. The reaction mixture is stirred for 2 days at room temperature and then poured onto 2 kg. of ice/water. The resulting mixture is extracted with diethyl ether and the extract is washed with water and dried over MgSO$_4$. The solvent is removed under vacuum and the residual liquid is distilled to give 83 g. (b.p. 116°–120° C./0.1 mm.) of product.

EXAMPLE 67

2-(p-Chlorophenoxy)-1-propanol O-methanesulfonate

A solution of 51.5 g of 2-(p-chlorophenoxy)-1-propanol and 57.5 ml of triethylamine in 680 ml of dichloromethane is chilled to −10° C. To the solution is added dropwise with stirring 25.8 ml of methanesulfonyl chloride in 20 ml of dichloromethane. The mixture is stirred for 1 hour at −7° C. to −10° C. and washed with ice cold water, saturated NaCl, saturated NaHCO$_3$ and dried (MgSO$_4$). The solvent is removed under reduced pressure to give 73 g of product as an oil.

EXAMPLE 68

Methyl{p-[2-(p-chlorophenoxy)propoxy[phenyl}acetate

An 11 g portion of sodium hydride (60% dispersion in oil) is washed with hexane under argon. To the sodium hydride is added 250 ml of N,N-dimethylacetamide and dropwise 46 g of methyl p-hydroxyphenylacetate in 90 ml of N,N-dimethylacetamide. The mixture is stirred one hour at room temperature and 20 minutes at 50° C. and a solution of 73 g of 2-(p-chlorophenoxy)-1-propanol O-methanesulfonate in 130 ml of N,N-dimethylacetamide added. The mixture is stirred and heated at 100° C. for 18 hours and poured into 2 liters of ice-water containing 40 ml of acetic acid. The mixture is extracted with ether and the extract washed with saturated NaHCO$_3$, saturated NaCl solution and dried (MgSO$_4$). The solvent is removed under reduced pressure to give 79.6 g of product as an oil. Crystallization from hexane-ether gives off-white crystals, mp 51°–53° C.

EXAMPLE 69

{p[2-(p-Chlorophenoxy)propoxy]phenyl}acetic acid

A mixture of 37.6 g of methyl{p-[2-(p-chlorophenoxy)propoxy]phenyl}acetate, 46 g of potassium hydroxide, 500 ml of water and 500 ml of ethanol is stirred and refluxed for 4 hours. The hot mixture is acidified with concentrated HCl, diluted with water and chilled. The mixture is extracted with dichloromethane and the extract washed with saturated sodium chloride and dried (MgSO$_4$). The solvent is removed under reduced pressure to give 31.6 g of product as a gum. Crystallization from hexane-ether gives tan crystals. Recrystallization from methanol-water gives white crystals, mp 88°–91° C.

EXAMPLE 70

Methyl bromo{p-[2-(p-chlorophenoxy)propoxy]phenyl}acetate

A solution of 17.3 g of {p-[2-(p-chlorophenoxy)propoxy]phenyl}acetic acid and 35 ml of thionyl chloride is refluxed for 1 hour. The mixture is concentrated under reduced pressure and benzene added (2 times) and the solvent removed. The residual oil is dissolved in 270 ml of carbon tetrachloride, 10.7 g of N-bromosuccinimide added and the mixture stirred and refluxed for 26 hours. The mixture is cooled, filtered and while cooling in an ice bath, 13 ml of methanol in 20 ml of carbon tetrachloride is added. The mixture is stirred for 1 hour and the solvent removed under reduced pressure. The residue is passed through a short column of silica gel with carbon tetrachloride as eluent (250 ml cuts). The first three cuts give 21.2 g of product as an oil.

EXAMPLE 71

Methyl(p-tert.-butylphenoxy){p-[2-(p-chlorophenoxy)propoxy]phenyl}acetate

To a solution of 2.55 g of p-tert.-butyophenol in 50 ml of tetrahydrofuran is added 0.68 g of sodium hydride (60% dispersion in oil). To the mixture is added 2.82 g of potassium iodide, 7.0 g of methyl bromo{p-[2-(p-chlorophenoxy)propoxy]phenyl}acetate in 25 ml of tetrahydrofuran. The mixture is heated at 80° C. for 18 hours and poured into 400 ml of ice-water containing 3 ml of acetic acid. The mixture is extracted with ethyl acetate and the extracts washed with saturated NaHCO$_3$, 10% sodium thiosulfate solution and dried (MgSO$_4$). The solvent is removed under reduced pressure to give 8.1 g of gum. The gum is dissolved in dichloromethane and chromatographed over silica gel to give 6.4 g of product as a gum.

EXAMPLE 72

Methyl(α,α,α-trifluoro-p-tolyoxy){p-[2-(p-chlorophenoxy)propoxy]phenyl}acetate

As described in Example 71, 2.75 g of α,α,α-trifluoro-p-cresol is reacted with 7.0 g of methyl bromo{p-[2-(p-chlorophenoxy)propoxy]phenyl}acetate to give 8.5 g of gum. The gum is chromatographed over silica gel with dichloromethane as eluent to give 6.6 g of product as a gum.

EXAMPLE 73

(p-tert.-Butylphenoxy){p-[2-(p-chlorophenoxy)propoxy]phenyl}acetic acid

A mixture of 6.4 g of methyl(p-tert.-butylphenoxy){p-[2-(p-chlorophenoxy)propoxy]phenyl}acetate, 4 g of potassium hydroxide, 35 ml of ethanol and 35 ml of water is refluxed for 4 hours. The mixture is acidified with concentrated HCl, cooled, diluted with water and extracted with dichloromethane. The extract is washed with saturated NaCl solution, dried (MgSO$_4$) and the solvent removed under reduced pressure to give 5.7 g of gum. Crystallization from hexane-ether gives 4.5 g of white crystals. Recrystallization from chloroform-hexane gives the product as white crystals, mp 135°–138° C.

EXAMPLE 74

Methyl(p-chlorophenoxy){p-[2-(p-chlorophenoxy)propoxy]phenyl}acetate

As described in Example 71, 2.19 g of p-chlorophenol is reacted with 7.0 g of methyl bromo{p-[2-(p-chlorophenoxy)propoxy]phenyl}acetate to give 6.2 g of product as a gum.

EXAMPLE 75

(p-Chlorophenoxy){p-[2-(p-chlorophenoxy)propoxy]phenyl}acetic acid

As described in Example 73, 6.2 g of methyl (p-chlorophenoxy){p-[2-(p-chlorophenoxy)propoxy]phenyl}acetate is hydrolyzed with 4 g of potassium hydroxide to give 5.91 g of gum. Crystallization from hexane-ether gives 4.73 g of off-white crystals. Recrystallization from chloroform-hexane gives white crystals, mp 146°–148° C.

EXAMPLE 76

(α,α,α-Trifluoro-p-tolyoxy){p-[2-(p-chlorophenoxy)propoxy]phenyl}acetic acid

As described in Example 73, 6.6 g of methyl(α,α,α-trifluoro-p-tolyoxy){p-[2-(p-chlorophenoxy)propoxy]phenyl}acetate is hydrolyzed with 4 g of potassium hydroxide to give 5.83 g of gum. Crystallization from hexane-ether gives 5.2 g of yellow crystals. Recrystallization from chloroform-hexane give white crystals, mp 127°–130° C.

EXAMPLE 77

2-(p-tert-Butylphenoxy)propionic acid

To a chilled slurry of 9.3 g of sodium hydride-oil dispersion (57%) in 150 ml of dimethyl sulfoxide is added 15.0 g of p-tert-butylphenol in 50 ml of dimethyl sulfoxide and 18.9 g of 2-bromopropionic acid in 50 ml of dimethyl sulfoxide. The mixture is stirred at room temperature for ½ hr. and heated on a steam bath overnight. The mixture is diluted with 250 ml of water, acidified with 10 ml of conc. hydrochloric acid and extracted with ether. The ether extracts are dried (MgSO$_4$) and the solvent removed under vacuum. Chromatography over silica gel with dichloromethane as eluent gives the product as white crystals, mp 86°–89° C.

EXAMPLE 78

2-(p-tert-Butylphenoxy)-1-propanol

A solution of 6.6 g of 2-(p-tert-butylphenoxy)propionic acid in 25 ml of tetrahydrofuran is added dropwise to a chilled (5° C.) solution of 60 ml of 1M diborane in tetrahydrofuran. The mixture is stirred for 1 hr at 5° C. and at room temperature overnight. The mixture is poured onto 300 g of ice-water and extracted with ether. The ether extracts are dried (MgSO$_4$) and concentrated under vacuum to give 5.5 g of product as a colorless liquid.

EXAMPLE 79

2-(p-tert-Butylphenoxy)-1-propanol O-methanesulfonate

As in Example 56, 5.1 g of 2-(p-tert-butylphenoxy)-1-propanol is reacted with 2.3 ml of methanesulfonyl chloride in 150 ml of dichloromethane in the presence of 8 ml of triethylamine. The product (7.4 g) is obtained as an amber-colored liquid.

EXAMPLE 80

Methyl Bromo{p-[2-(p-tert-Butylphenoxy)propoxy]phenyl}acetate

As described in Example 68, 46 g of methyl p-hydroxy-phenylacetate is reacted with 2-(p-tert-butylphenoxy)-1-propanol O-methanesulfonate in 400 ml of N,N-dimethylacetamide to give the product as a viscous oil. A sample of this product (0.05 mole) is dissolved in 250 ml of carbon tetrachloride and N-bromosuccinimide (10 g) added. To the mixture is added anhydrous HBr and the mixture refluxed for 24 hr. The mixture is filtered through a short column of silica gel and the solvent removed under vacuum to give the product as a viscous oil.

EXAMPLE 81

Methyl(α,α,α,-Trifluoro-m-tolyloxy){p-[2-(p-tert-butylphenoxy)propoxy]phenyl}acetate As described in Example 71, methyl bromo{p-[2-(p-tert-butylphenoxy)propoxy]phenyl}acetate (0.017 mole) is reacted with 2.75 g of α,α,α,-trifluoro-m-cresol in 75 ml of tetrahydrofuran at 80° C. for 18 hrs to give the product as a pale yellow gum.

EXAMPLE 82

Methyl(p-tert-Butylphenoxy){p-[2-(p-tert-Butylphenoxy)propoxy]phenyl}acetate

As described in Example 71, methyl bromo{p-[2-(p-tert-butylphenoxy)propoxy]phenyl}acetate (0.017 mole) is reacted with 2.55 g of p-tert-butylphenol in 75 ml of tetrahydrofuran at 80° C. for 18 hr to give the product as a gum.

EXAMPLE 83

Methyl(α,α,α-trifluoro-p-tolyloxy)-{p-[2-(p-tert-butylphenoxy)propoxy]phenyl}acetate As described in Example 71, methyl bromo{p-[2-(p-tert-butylphenoxy)propoxy]phenyl}acetate (0.017 mole) is reacted with 2.75 g of α,α,α-trifluoro-p-cresol in 75 ml of tetrahydrofuran at 80° C. for 24 hrs to give the product as a gum.

EXAMPLE 84

2-(p-Fluorophenoxy)propionic acid

To a stirred slurry of 8.3 g of sodium hydride (57° 10 NaH in oil) in 100 ml of dry 1,2-dimethoxyethane at 5° C. is added 15.3 g of 2-bromopropionic acid in 50 ml of 1,2-dimethoxyethane and 10.5 g of 4-fluorophenol in 50 ml of 1,2-dimethoxyethane. The mixture is refluxed for 6 hrs, cooled and filtered. The solid is partitioned between dichloromethane and 1N HCl. The organic layer is dried (MgSO₄) and concentrated to 50 ml. The mixture is filtered to give 10.4 g of product, mp 113°–115° C.

EXAMPLE 85

2-(p-Fluorophenoxy)-1-propanol

To 95 ml of 1 Molar diborane in tetrahydrofuran is added 10.2 g of 2-(p-fluorophenoxy)propionic acid in 100 ml of tetrahydrofuran. The mixture is stirred at room temperature for 20 hrs. and poured onto 600 g of ice. The mixture is extracted with chloroform and the chloroform extracts dried (MgSO₄). The solvent is removed under vacuum and the residual liquid distilled to give 8.7 g of colorless liquid.

EXAMPLE 86

2-(p-Fluorophenoxy)-1-propanol O-methanesulfonate

As described in Example 56, 7.7 g of 2-(p-fluorophenoxy)-1-propanol is reacted with 8.8 ml of methanesulfonyl chloride in 400 ml of dichloromethane in the presence of 12.5 ml of triethylamine. The product is obtained as a pale yellow liquid.

EXAMPLE 87

Methyl Bromo{p-[2-(p-fluorophenoxy)propoxy]phenyl}acetate

As described in Example 68, 46 g of methyl p-hydroxyphenylacetate is reacted with 2-(p-Fluorophenoxy)-1-propanol O-methane-sulfonate in 400 ml of N,N-dimethylacetamide at 100° C. for 18 hrs. The product is dissolved in 1250 ml of carbon tetrachloride and N-bromosuccinimide added. Anhydrous HBr is added and the mixture is stirred and refluxed for 24 hrs. The mixture is filtered through a short column of silica gel and the solvent removed to give the product as a viscous oil.

EXAMPLE 88

Methyl (p-tert-Butylphenoxy){p-[2-(p-fluorophenoxy)propoxy]phenyl}acetate

As described in Example 71, methyl bromo{p-[2-(p-fluorophenoxy)propoxy]phenyl}acetate (0.017 mole) is reacted with 2.55 g of p-tert-butylphenol in 75 ml of tetrahydrofuran at 80° C. for 18 hrs to give the product as a gum.

EXAMPLE 89

Methyl (α,α,α-Trifluoro-p-tolyloxy){p-[2-(p-fluorophenoxy)propoxy]phenyl}acetate As described in Example 71, methyl bromo{p-[2-(p-fluorophenoxy)propoxy]phenyl}acetate (0.017 mole) is reacted with 2.75 g of α,α,α-trifluoro-p-cresol in 75 ml of tetrahydrofuran at 80° C. for 18 hrs to give the product as a pale amber gum.

EXAMPLE 90

Methyl (p-Phenoxyphenoxy){p-[2-(p-fluorophenoxy)propoxy]phenyl}acetate

As described in Example 35, 4.66 g of p-phenoxyphenol is reacted with methyl bromo{p-[2-(p-fluorophenoxy)propoxy]phenyl}acetate (0.02 mole) in refluxing methanol-benzene for 24 hrs to give the product as a viscous oil.

EXAMPLE 91

Methyl (p-Isopropylphenoxy){p-[2-(p-fluorophenoxy)propoxy]phenyl}acetate

As described in Example 71, methyl bromo{p-[2-(p-fluorophenoxy)propoxy]phenyl}acetate (0.017 mole) is reacted with p-isopropylphenol (0.017 mole) in 75 ml of tetrahydrofuran at 80° C. for 18 hrs to give the product as a viscous oil.

EXAMPLE 92

2-(α,α,α-Trifluoro-p-tolyloxy)propionic acid

To a slurry of 12 g of sodium hydride-oil dispersion (57%) in 100 ml of N,N-dimethylformamide is added 21 g of α,α,α-trifluoro-p-cresol in 10 ml of dimethylformamide and 24 g of 2-bromopropionic acid. After hydrogen evolution, the mixture is heated at 90° C. for 14 hrs. The mixture is cooled, diluted with 100 ml of water, acidified with hydrochloric acid and extracted with ether. The ether extracts are dried (MgSO₄) and concentrated to give 23 g of product. A 3.5 g sample is chromatographed over silica gel with solvent hexane-ether-acetic acid (80:20:1) to give 2.3 g of white crystals. Recrystallization from hexane gives crystals, mp 81°–82° C.

EXAMPLE 93

2-(α,α,α-Trifluoro-p-tolyloxy)-1-propanol

To 150 ml of 1M diborane in tetrahydrofuran is added 13.5 g of 2-(α,α,α-trifluoro-p-tolyloxy)propionic acid. The mixture is stirred at room temperature for 6 hrs and poured onto 400 g of ice-water. The mixture is extracted with ether and the extract dried (MgSO$_4$) and concentrated to give 14.6 g of colorless liquid. Distillation gives 8.1 g of liquid which crystallizes to give product, mp 29°–32° C.

EXAMPLE 94

2-(α,α,α-Trifluoro-p-tolyloxy)-1-propanol O-methanesulfonate

As per Example 56, 7.95 g of 2-(α,α,α-trifluoro-p-tolyloxy)-1-propanol is reacted with 4.7 g of methanesulfonyl chloride in 100 ml of dichloromethane in the presence of 7.3 g of triethylamine. The product (10.92) is obtained as a pale yellow liquid.

EXAMPLE 95

Methyl Bromo {p-[2-(α,α,α-trifluoro-p-tolyloxy)propoxy]phenyl}acetate

As described in Example 68, 46 g of methyl p-hydroxyphenylacetate is reacted with 2-(α,α,α-trifluoro-p-tolyloxy)-1-propanol O-methanesulfonate in 400 ml of N,N-dimethylacetamide at 100° C. for 18 hrs. The product as an oil is dissolved in 12.50 ml of carbon tetrachloride and N-bromosuccinimide is added. Anhydrous HBr is added and the mixture is stirred and refluxed for 24 hrs. The mixture is filtered through a short column of silica gel and the solvent removed to give the product as an oil.

EXAMPLE 96

Methyl (p-tert-Butylphenoxy){p-[2-(α,α,α-trifluoro-p-tolyloxy)propoxy]phenyl acetate As described in Example 71, 2.55 g of p-tert-butylphenol is reacted with methyl bromo{p-[2-(α,α,α-trifluoro-p-tolyloxy)propoxy]phenyl}acetate (0.017 mole) in 75 ml of tetrahydrofuran at 80° C. for 18 hrs to give the product as a viscous oil.

EXAMPLE 97

Methyl (α,α,α-Trifluoro-m-tolyloxy){p-[2-(α,α,α-trifluoro-p-tolyloxy)propoxy)phenyl}acetate As described in Example 71, methyl bromo{p-[2(α,α,α-trifluoro-p-tolyloxy)propoxy]phenyl}acetate (0.017 mole) is reacted with 2.75 g of α,α,α-trifluoro-m-cresol in 75 ml of tetrahydrofuran at 80° C. for 18 hrs to give the product as a viscous oil.

EXAMPLE 98

Methyl (p-Phenoxyphenoxy){p-[2-(α,α,α-Trifluoro-p-tolyloxy)propoxy]phenyl}acetate As described in Example 35, 4.66 of p-phenoxyphenol is reacted with methyl bromo{p-[2-(α,α,α-trifluoro-p-tolyloxy)propoxy]phenyl}acetate (0.02 mole) in refluxing methanol-benzene for 24 hrs to give the product as a gum.

EXAMPLE 99

Methyl (α,α,α-Trifluoro-p-tolyloxy){p-[2-(α,α,α-trifluoro-p-tolyloxy)propoxy]phenyl}acetate As described in Example 71, methyl bromo{p-[2-(α,α,α-trifluoro-p-tolyloxy)propoxy]phenyl}acetate (0.017 mole) is reacted with 2.75 g of α,α,α-trifluoro-p-cresol in 75 ml of tetrahydrofuran at 80° C. for 24 hrs to give the product as a viscous oil.

EXAMPLE 100

2-(p-Fluorophenoxy)ethanol

To 200 ml of 1 Molar diborane in tetrahydrofuran (chilled to 5°–10° C.) is added dropwise 17.0 g of 2-(p-fluorophenoxy)acetic acid in 100 ml of tetrahydrofuran. The mixture is stirred overnight and poured into 100 g of ice and 250 ml of chloroform. The organic layer is separated and the aqueous layer extracted with chloroform. The organic layer and extracts are combined, dried (MgSO$_4$) and the solvent removed under vacuum. The residual pale yellow oil is distilled to give the product (14.8 g) as a colorless oil.

EXAMPLE 101

2-(p-Fluorophenoxy)ethanol O-methanesulfonate

As for Example 56, 12.5 g of 2-(p-fluorophenoxy)ethanol is reacted with 7 ml of methanesulfonyl chloride in 100 ml of dichloromethane in the presence of 23 ml of triethylamine. The product (18 g) is obtained as a colorless liquid.

EXAMPLE 102

Methyl Bromo {p-[2-(p-fluorophenoxy)ethoxy]phenyl}acetate

As described in Example 17, 58.5 g of methyl p-hydroxyphenylacetate in 500 ml of N,N-dimethylacetamide is reacted with 2-(p-fluorophenoxy)ethanol O-methanesulfonate (0.35 mole) at 100° C. for 18 hrs to give an off-white solid. The solid is dissolved in 1500 ml of carbon tetrachloride and N-bromosuccinimide added. Anhydrous HBr is added and the mixture is stirred and refluxed for 24 hrs. The mixture is passed through a short column of silica gel and the solvent removed to give the product.

EXAMPLE 103

Methyl (p-tert-Butylphenoxy){p-[2-(p-fluorophenoxy)ethoxy]phenyl acetate

As described in Example 71, methyl bromo{p-[2-(p-fluorophenoxy)propoxy]phenyl}acetate (0.017 mole) is reacted with 2.55 g of p-tert-butylphenol in 75 ml of tetrahydrofuran at 80° C. for 18 hrs to give the product.

EXAMPLE 104

Methyl (α,α,α-Trifluoro-p-tolyloxy) p-[2-(p-fluorophenoxy) ethoxy]phenyl acetate As described in Example 71, methyl{bromo p-[2-(p-fluorophenoxy)propoxy]phenyl}acetate (0.017 mole) is reacted with 2.75 g of α,α,α-trifluoro-p-cresol in 75 ml of tetrahydrofuran at 80° C. for 18 hrs to give the product as a gum.

EXAMPLE 105

Methyl (p-Phenoxyphenyl){p-[2-(p-fluorophenoxy)ethoxy]phenyl}acetate

As described in Example 35, 4.66 g of p-phenoxyphenol is reacted with methyl bromo{p-[2-(p-fluorophenoxy)propoxy]phenyl}acetate (0.02 mole) in refluxing methanol-benzene for 24 hrs to give the product as a viscous oil.

EXAMPLE 106

Methyl (3,4-Dimethylphenoxy){p-[2-(p-fluorophenoxy)ethoxy]phenyl}acetate

As described in Example 71, methyl bromo{p-[2-(p-fluorophenoxy)ethoxy]phenyl}acetate (0.017 mole) is reacted with 3,4-dimethylphenol (0.017 mole) in 75 ml of tetrahydrofuran at 80° C. for 18 hrs to give the product as a gum.

EXAMPLE 107

Methyl (p-Isopropylphenoxy){p-[3-(p-chlorophenoxy)propoxy]phenyl}acetate

As described in Example 71, 7.9 g of methyl bromo{p-[3-(p-chlorophenoxy)propoxy]phenyl}acetate is reacted with 2.86 g of p-isopropylphenol in 75 ml of tetrahydrofuran at 80° C. for 18 hrs to give the product as a solid.

We claim:

1. A compound selected from the group consisting of those of the formula:

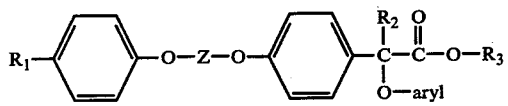

wherein $R_1$ is fluoro, chloro, trifluoromethyl or tert.-butyl; $R_2$ is hydrogen or straight chain alkyl having up to 6 carbon atoms; $R_3$ is hydrogen or alkyl having up to 4 carbon atoms; Z is a divalent radical selected from the group consisting of those of the formulae:

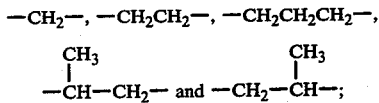

and aryl is selected from the group consisting of 3,4-dimethylphenyl, 3-methyl-4-chlorophenyl, 2-chloro-4-tert.-butylphenyl, 5-indanyl, 5,6,7,8-tetrahydro-2-naphthyl and moieties of the formulae:

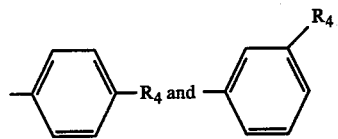

wherein $R_4$ is hydrogen, chloro, cyano, alkyl having up to 4 carbon atoms, trifluoromethyl, phenoxy, benzyloxy or cyclohexyl; and the pharmacologically acceptable cationic salts thereof when $R_3$ is hydrogen.

2. The compound according to claim 1 wherein $R_1$ is chloro, $R_2$ is hydrogen, $R_3$ is methyl, Z is —$CH_2$—, and aryl is p-tert-butylphenyl; methyl (p-tert-butylphenoxy){p-[(p-chlorophenoxy)methoxy]phenyl}acetate.

3. The compound according to claim 1 wherein $R_1$ is tert.-butyl, $R_2$ is methyl, $R_3$ is ethyl, Z is —$CH_2$—, and aryl is m-trifluoromethylphenyl; ethyl 2-($\alpha,\alpha,\alpha$-trifluoro-m-tolyloxy)-2-{p-[-tert.-butyl-phenoxy)methoxy]phenyl}propionate.

4. The compound according to claim 1 wherein $R_1$ is chloro, $R_2$ is hydrogen, $R_3$ is hydrogen, Z is —$CH_2CH(CH_3)$—, and aryl is p-tert-butylphenyl; 2-(p-tert-butylphenoxy)-2-{p-[2-(p-chlorophenoxy)-1-methylethoxy]phenyl}acetic acid.

5. The compound according to claim 1 wherein $R_1$ is chloro, $R_2$ is hydrogen, $R_3$ is ethyl, Z is —$CH(CH_3)CH_2$—, and aryl is p-tert-butylphenyl; ethyl 2-(p-tert-butylphenoxy)-2-{p-[2-(p-chlorophenoxy)propoxy]phenyl}acetate.

6. The compound according to claim 1 wherein $R_1$ is chloro, $R_2$ is hydrogen, $R_3$ is ethyl, Z is —$(CH_2)_3$—, and aryl is p-tert-butylphenyl; ethyl 2-(tert-butylphenoxy)-2-{p[3-(p-chlorophenoxy)propoxy]phenyl}acetate.

7. The compound according to claim 1 wherein $R_1$ is chloro, $R_2$ is n-butyl, $R_3$ is ethyl, Z is —$(CH_2)_3$—, and aryl is p-tert-butylphenyl; ethyl 2-(p-tert-butylphenoxy)-2-{p-[3-(p-chlorophenoxy)propoxy]phenyl}-n-caproate.

8. The compound according to claim 1 wherein $R_1$ is fluoro, $R_2$ is hydrogen, $R_3$ is ethyl, Z is —$CH(CH_3)CH_2$—, and aryl is p-tert-butylphenoxy; ethyl 2-(p-tert-butylphenoxy)-2-{p-[2-(p-fluorophenoxy)propoxy]phenyl}acetate.

9. The compound according to claim 1 wherein $R_1$ is chloro, $R_2$ is hydrogen, $R_3$ is hydrogen, Z is —$CH_2$—, and aryl is 3,4-dimethylphenyl; 2-(3,4-dimethylphenoxy)-2-{p-[(p-chlorophenoxy)methoxy]phenyl}acetic acid.

10. The compound according to claim 1 wherein $R_1$ is chloro, $R_2$ is hydrogen, $R_3$ is ethyl, Z is —$(CH_2)_2$—, and aryl is p-trifluoromethylphenyl; ethyl 2-($\alpha,\alpha,\alpha$-trifluoro-p-tolyloxy)-2-{p-[chlorophenoxy)ethoxy]phenyl}acetate.

11. The compound according to claim 1 wherein $R_1$ is chloro, $R_2$ is hydrogen, $R_3$ is ethyl, Z is —$CH_2CH(CH_3)$—, and aryl is p-trifluoromethylphenyl; ethyl 2-($\alpha,\alpha,\alpha$-trifluoro-p-tolyloxy)-2-{p-[2-(p-chlorophenoxy)-1-methylethoxy]phenyl} acetate.

12. The compound according to claim 1 wherein $R_1$ is chloro, $R_2$ is methyl, $R_3$ is hydrogen, Z is —$(CH_2)_3$—, and aryl is p-tert-butylphenyl; 2-(p-tert-butylphenoxy)-2-{p-[3-(p-chlorophenoxy)propoxy]phenyl}propionic acid.

13. The compound according to claim 1 wherein $R_1$ is chloro, $R_2$ and $R_3$ are hydrogen, Z is —$(CH_2)_3$—, and aryl is p-tert-butylphenyl; 2-(p-tert-butylphenoxy)-2-{p-[3-(p-chlorophenoxy)propoxy]phenyl}acetic acid.

* * * * *